(12) United States Patent
Lambris et al.

(10) Patent No.: US 9,358,266 B2
(45) Date of Patent: Jun. 7, 2016

(54) TREATMENT OF SEPSIS USING COMPLEMENT INHIBITORS

(75) Inventors: John D. Lambris, Philadelphia, PA (US); Fletcher B. Taylor, Pinetops, NC (US); Florea Lupu, Oklahoma City, OK (US); Gary Kinasewitz, Edmond, OK (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 13/580,821

(22) PCT Filed: Feb. 25, 2011

(86) PCT No.: PCT/US2011/026229
§ 371 (c)(1),
(2), (4) Date: Nov. 12, 2012

(87) PCT Pub. No.: WO2011/106635
PCT Pub. Date: Sep. 1, 2011

(65) Prior Publication Data
US 2013/0053302 A1    Feb. 28, 2013

Related U.S. Application Data

(60) Provisional application No. 61/308,094, filed on Feb. 25, 2010.

(51) Int. Cl.
*A61K 38/12* (2006.01)
*A61P 29/00* (2006.01)
*A61K 38/10* (2006.01)

(52) U.S. Cl.
CPC ..................................... *A61K 38/10* (2013.01)

(58) Field of Classification Search
None
See application file for complete search history.

(56) References Cited

U.S. PATENT DOCUMENTS

| | | | |
|---|---|---|---|
| 6,180,370 B1 | 1/2001 | Queen et al. |
| 6,319,897 B1 | 11/2001 | Lambris et al. |
| 7,888,323 B2 | 2/2011 | Lambris et al. |
| 2003/0224490 A1 | 12/2003 | Dessain et al. |
| 2006/0217530 A1 | 9/2006 | Maxwell et al. |
| 2007/0274989 A1 | 11/2007 | Fung et al. |
| 2008/0233113 A1 | 9/2008 | Bansal |
| 2010/0015139 A1 | 1/2010 | Bansal |

FOREIGN PATENT DOCUMENTS

| WO | WO 9913899 | 3/1999 |
|---|---|---|
| WO | WO 0115731 | 3/2001 |
| WO | WO 2004026328 | 4/2004 |
| WO | WO 2004/103294 A2 * | 12/2004 |
| WO | WO 2004103294 | 12/2004 |
| WO | WO 2006125200 | 11/2006 |
| WO | WO 2009/015087 | 1/2009 |
| WO | WO 2010127336 | 11/2010 |

OTHER PUBLICATIONS

Taylor et al., Protein C Prevents the Coagulopathic and Lethal Effects of *Escherichia coli* Infusion in the Baboon., J. Clin. Invest. vol. 79, Mar. 1987, pp. 918-925.*
Zeerleder et al. (Clin. Diagn. Lab, 2003, 10(4):529).*
Caliezi et al. (Critical Care Medicine 30(8); Aug. 2002, pp. 1722-1728).*
Mollines et al. (Strategies of therapeutic complement inhibition; Molecular Immunology 43 (2006) 107-121).*
Bellows et al., New Compstatin Variants Through Two De Novo Protein Design Frameworks, Biophysical Journal, vol. 98, No. 10, pp. 2337-2346, May 2010.
Bengtsson, A. et al., Complement and Leukocyte Activation in Septic Baboons, Circ Shock. 39: 83-88, 1993.
Bhole, et al., Therapeutic potential of targeting the complement cascade in critical care medicine, , Crit Care Med. 31: S97-S104, 2003.
Bird et al., Single Chain Antigen-Binding Proteins, Science 242:423-426, 1988.
Brekke, et al., Combined Inhibition of Complement and CD14 Abolish *E. coli*-Induced Cytokine-,Chemokine- and Growth Factor-Synthesis in Human Whole Blood, Molecular Immunology, vol. 45, No. 14, pp. 3804-3813, Aug. 1, 2008.
Brekke, et al.,The Role of Complement C3 Opsonization, C5a Receptor,and CD14 in *E. coli*-induced up-Regulation of Granulocyte and Monocyte CD11b/CD18 (CR3),• Phagocytosis, and Oxidative Burst in Human Whole Blood, Journal OfLeukocyte Biology, vol. 81, No. 6, pp. 1404-1413, Jun. 2007.
Burton et al., Human Antibodies From Combinatorial Libraries, Adv. lmmunol. 57:191-280, 1994.
De Boer JP, et al., Activation of the Complement System in Baboons Challenged With Live *Escherichia coli*: Correlation With Mortality and Evidence for a Biphasic Activation Pattern, Infect Immun. 61: 4293-4301, 1993.
Gu et al., Construction and Expression of Mouse-Human Chimeric Antibody SZ-51 Specific for Activated Platelet P-Selectin, Thromb. Hema., vol. 77, pp. 755-759, 1997.
Hellerud,et al., Stages of Meningococcal Sepsis Simulated in Vitro, With Emphasis on Complement and Toll-like Receptor Activation, Infection and Immunity, vol. 76, No. 9, pp. 4183-4189, Sep. 2008.

(Continued)

*Primary Examiner* — James H Alstrum Acevedo
*Assistant Examiner* — Tara Martinez
(74) *Attorney, Agent, or Firm* — Potter Anderson and Corroon LLP

(57) ABSTRACT

Methods for the treatment of sepsis with complement inhibitors are disclosed. In particular, C3 inhibitors, such as Compstatin and Compstatin analogs, are administered at various times following the onset of sepsis to alleviate tissue damage and organ failure, which are hallmarks of the second, extravascular stage of sepsis. Combination therapies for comprehensive treatment of sepsis are also disclosed. Pharmaceutical compositions and kits for use in the methods are disclosed as well.

11 Claims, 7 Drawing Sheets

(56) References Cited

OTHER PUBLICATIONS

Houston et al., Protein Engineering of Antibody Binding Sites: Recovery of Specific Activity in an Anti-Digoxin Single-Chain Fv Analogue Produced in *Escherichia coli*, Proc. Natl. Acad. Sci. 85:5879-5883, 1988.

Katragadda et al., Hydrophobic Effect and Hydrogen Bonds Account for the Improved Activity of a Complement Inhibitor, Compstatin, J Med Chem. 49: 4616-4622, 2006.

Laudes, I.J., et al., Anti-c5a Ameliorates Coagulation/fibrinolytic Protein Changes in a Rat Model of Sepsis, Am. J. Pathol. 160: 1867-1875, 2002.

Liu et al., C1 Inhibitor-Mediated Protection from Sepsis, Journal of Immunology, vol. 179, No. 6, pp. 3966-3972, (Sep. 15, 2007).

Markiewski et al., Complexity of Complement Activation in Sepsis, J Cell Mol Med. 12: 2245-2254, 2008.

Markiewski et al., The Role of Complement in Inflammatory Diseases From Behind the Scenes Into the Spotlight, Am J Pathol. 171: 715-727, 2007.

Proctor et al., Transdermal Pharmacology of Small Molecule Cyclic C5a antagonists, Adv Exp Med Biol. 586:329-45, 2006.

Proctor et al., "Complement Inhibitors Selectively Attenuate Injury Following Administration of Cobra Venom Factor to Rats", International Immunopharmacology, vol. 6, pp. 1224-1232, 2006.

Qu et al., Novel Analogues of the Therapeutic Complement Inhibitor Compstatin with Significantly Improved Affinity and Potency, Molecular Immunology, vol. 48, No. 4, pp. 481-489, 2011.

Sahu A, et al., Compstatin, a Peptide Inhibitor of Complement, Exhibits Species-Specific Binding to Complement Component C3, *Molec. Immunol.* 39: 557-566, 2003.

Silasi-Mansat et al., Complement Inhibition Decreases the Procoagulant Response and Confers Organ Protection in a Baboon Model of *Escherichia coli* Sepsis: Blood, Am Soc. of Hematology, US, vol. 116, No. 6, pp. 1002-1010, Aug. 12, 2010.

Stahl GL, et al., Role for the Alternative Complement Pathway in Ischemia/Reperfusion Injury, Am J Pathol. 162: 449-455, 2003.

Tang et al., Sepsis-Induced Coagulation in the Baboon Lung ss Associated With Decreased Tissue Factor Pathway Inhibitor, *Am J Pathol.* 171: 1066-1077, 2007.

Taylor FB, Jr., et al., The Endothelial Cell Protein C Receptor Aids in Host Defense Against *Escherichia coli* sepsis, Blood 95: 1680-1686, 2000.

Taylor, et al., Observations on Complement Activity in the Two-Stage Inflammatory/Hemostatic Response in the Baboon and Human Models of *E. coli* Sepsis and Endotoxemia, Adv Exp Med Biol. 586: 203-216, 2006.

Taylor FB, Jr., Staging of the Pathophysiologic Responses of the Primate Microvasculature to *Escherichia coli* and Endotoxin: Examination of the Elements of the Compensated Response and Their Links to the Corresponding Uncompensated Lethal Variants, *Crit Care Med.* 29: S78-89, 2001.

Thorgersen et al., "Inhibition of Complement and CD14 Attenuates the *Escherichia coli*-Induced Inflammatory Response in Porcine Whole Blood", Infection and Immunity, vol. 77, No. 2, pp. 725-732, Feb. 2009.

Tuszynski et al., Thrombospondin Promotes Platelet Aggregation, Blood, 72:109-115, 1988.

Ward PA, The Dark Side of C5a in Sepsis, Nat Rev Imrnunol. 4: 133-142, 2004.

Wright, A. et al., Genetically Engineered Antibodies: Progress and Prospects, *Critical Rev. Immunol.* 12(3,4):125-168, 1992.

Xu, J et al., Extracellular Histones are Major Mediators of Death in Sepsis, Nature Med. 15: 1318-1322, 2009.

International Search Report and Written Opinion in PCT/US2011/026229, mailed May 4, 2011.

\* cited by examiner

SEQUENCE LISTING

```
<160> NUMBER OF SEQ ID NOS: 4

<210> SEQ ID NO 1
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (2)..(12)

<400> SEQUENCE: 1

Ile Cys Val Val Gln Asp Trp Gly His His Arg Cys Thr
1               5                   10

<210> SEQ ID NO 2
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is Gly or is missing
<220> FEATURE:
<221> NAME/KEY: VARIANT
<222> LOCATION: (2)..(2)
<223> OTHER INFORMATION: Xaa is Ile, Val, Leu, Ac-Ile, Ac-Val or Ac-Leu
<220> FEATURE:
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Xaa is Trp or an analog of Trp
<220> FEATURE:
```

```
<221> NAME/KEY: VARIANT
<222> LOCATION: (10)..(10)
<223> OTHER INFORMATION: Xaa is His, Ala, Phe or Trp
<220> FEATURE:
<221> NAME/KEY: VARIANT
<222> LOCATION: (14)..(14)
<223> OTHER INFORMATION: Xaa is L-Thr, D-Thr, Ile, Val or Gly
<220> FEATURE:
<221> NAME/KEY: VARIANT
<222> LOCATION: (15)..(15)
<223> OTHER INFORMATION: Xaa is Asn or Ala, or is missing
<220> FEATURE:
<221> NAME/KEY: VARIANT
<222> LOCATION: (16)..(16)
<223> OTHER INFORMATION: Xaa is Asn, or is missing

<400> SEQUENCE: 2

Xaa Xaa Cys Val Xaa Gln Asp Trp Gly Xaa His Arg Cys Xaa Xaa Xaa
 1               5                  10                  15

<210> SEQ ID NO 3
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is Gly or is missing
<220> FEATURE:
<221> NAME/KEY: VARIANT
<222> LOCATION: (2)..(2)
<223> OTHER INFORMATION: Xaa is Ile, Val, Leu, Ac-Ile, Ac-Val or Ac-Leu
<220> FEATURE:
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Xaa is Trp or an analog of Trp
<220> FEATURE:
<221> NAME/KEY: VARIANT
<222> LOCATION: (8)..(8)
<223> OTHER INFORMATION: Xaa is Trp or an analog of Trp
<220> FEATURE:
<221> NAME/KEY: VARIANT
<222> LOCATION: (10)..(10)
<223> OTHER INFORMATION: Xaa is His, Ala, Phe or Trp
<220> FEATURE:
<221> NAME/KEY: VARIANT
<222> LOCATION: (14)..(14)
<223> OTHER INFORMATION: Xaa is L-Thr, D-Thr, Ile, Val or Gly
<220> FEATURE:
<221> NAME/KEY: VARIANT
<222> LOCATION: (15)..(15)
<223> OTHER INFORMATION: Xaa is Asn or Ala, or is missing
<220> FEATURE:
<221> NAME/KEY: VARIANT
<222> LOCATION: (16)..(16)
<223> OTHER INFORMATION: Xaa is Asn, or is missing

<400> SEQUENCE: 3

Xaa Xaa Cys Val Xaa Gln Asp Xaa Gly Xaa His Arg Cys Xaa Xaa Xaa
 1               5                  10                  15

<210> SEQ ID NO 4
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: 1-methyl Tryptophan
<220> FEATURE:
<221> NAME/KEY: MOD_RES
<222> LOCATION: (13)..(13)
<223> OTHER INFORMATION: AMIDATION

<400> SEQUENCE: 4

Ile Cys Val Trp Gln Asp Trp Gly Ala His Arg Cys Thr
1               5                   10
```

TREATMENT OF SEPSIS USING COMPLEMENT INHIBITORS

This invention was made with government support under Grant Nos. AL068730 and GM-62134 awarded by the National Institutes of Health. The government has certain rights in the invention.

FIELD OF THE INVENTION

This invention relates to the treatment of sepsis with complement inhibitors. In particular, methods focusing on the extravascular elements of sepsis are provided. Combination therapies are also provided for comprehensive treatment of sepsis.

BACKGROUND OF THE INVENTION

Various publications, including patents, published applications, technical articles and scholarly articles are cited throughout the specification. Each of these cited publications is incorporated by reference herein, in its entirety. Full citations for publications not cited fully within the specification are set forth at the end of the specification.

Severe sepsis is a multi-stage, multi-factorial and life threatening clinical syndrome that arises through the innate response to infection, and can appear as a complication in conditions like trauma, cancer and surgery. Despite important strides made in understanding its pathophysiology, the sepsis-related mortality and morbidity rates remain unacceptably high. Sepsis affects about 700,000 people and accounts for about 210,000 deaths per year in the United States alone.

In its most fulminate form, sepsis can produce cardiovascular collapse and death within hours. This variant of sepsis is almost always fatal in about 15% of patients receiving this diagnosis. More common is the development of multi-organ failure (MOF) secondary to hypoperfusion, histone release and intravascular thrombosis. In these variants of sepsis, MOF may be progressive and run a protracted clinical course, eventually proving fatal in 30-40% of patients. A variant of sepsis, affecting the remaining 30-40% of patients, involves a non-progressive MOF, in which the patient's condition can remain stable or improve during the first 48 hours of sepsis. Though they do not die, patients with this variant of sepsis can suffer long-term residual disabilities resulting from the sepsis-related tissue and organ damage.

The mechanisms responsible for the persistent and progressive or non-progressive organ failure are not fully understood. To examine this problem, non-human primate models of $E.$ $coli$ sepsis have been developed, which, depending on the bacterial dose, mimic the different pathophysiological syndromes observed in clinical practice (Taylor F B, Jr. 2001, $Crit$ $Care$ $Med.$ 29: S78-89). Challenge with $10^{10}$ cfu/kg $E.$ $coli$ ($LD_{100}$) results in an explosive inflammatory and coagulopathic response leading to irreversible shock and death. The administration of a lower dose, $10^9$ cfu/kg $E.$ $coli$ ($LD_{50}$) produces transient hypotension followed by MOF, which may progress and prove fatal in approximately 50% of the animals. Administration of still lower concentrations, $10^{7-8}$ cfu/kg $E.$ $coli$ ($LD_{10}$), produces a transient hypotension followed by MOF of less severity, which typically resolves in most patients, though residual long-term organ damage may result.

The pathophysiology of the $LD_{50}$ model in particular demonstrates a two-stage or two-compartment response, each driven by distinct mechanisms. The first stage is an exacerbated intravascular host defense response to bacterial infection while the second stage is an uncontrolled extravascular host recovery response, which is believed to be driven at least in part by ischemia-reperfusion (IR) injury, leading to MOF. It is believed that both stages occur in the more severe ($LD_{100}$) and the less severe ($LD_{10}$) models of sepsis. However, in the $LD_{100}$ model, the two stages overlap greatly, making it difficult to distinguish the two as having separate etiologies. Conversely, in the $LD_{10}$ model, the biomarkers associated with both stages of sepsis are present, but are less evident due to the comparatively mild symptomology. Sepsis-induced release of histones into the blood has also been shown recently to be a major mediator of death in two animal models of sepsis (Xu, J et al., 2009, $Nature$ $Med.$ 15: 1318-1322).

Complement is critical for the innate immunity against pathogens, but uncontrolled complement activation has been associated with many immuno-inflammatory conditions (Markiewski M M et al., 2008, $J$ $Cell$ $Mol$ $Med.$ 12: 2245-2254). All three complement activation pathways, the classical (CP), the lectin (LP) and the alternative (AP), converge at C3, which is cleaved by CP-, LP- and AP-generated C3 convertases to C3a and C3b. The anaphylatoxin C3a activates platelets, induces their aggregation and recruits leukocytes. C3b participates in the formation of C5 convertase, which cleaves C5 to C5a and C5b, the latter becoming part of the terminal C5b-9 complex (TCC) (Markiewski M M & Lambris J D, 2007, $Am$ $J$ $Pathol.$ 171: 715-727). Elevated levels of C5a could signal through its receptors C5aR and C5L2, contributing to immune paralysis, multi-organ dysfunction, apoptosis, deterioration of the coagulation/fibrinolytic system and contractile dysfunction of the cardiomyocytes (Ward P A, 2004, $Nat$ $Rev$ $Immunol.$ 4: 133-142). Researchers have described a biphasic activation of the complement cascade in response to sublethal $E.$ $coli$ in baboons, with maximum peak of complement activation products occurring during the second stage (de Boer J P, et al., 1993, $Infect$ $Immun.$ 61: 4293-4301; Taylor F B, Jr., et al., 2006, $Adv$ $Exp$ $Med$ $Biol.$ 586: 203-216). It has been suggested that early increase of complement activation during sepsis may relate to bacteria opsonization (de Boer et al., 1993, supra; Bengtsson A, et al., 1993, $Circ$ $Shock.$ 39: 83-88), thus being beneficial in the host defense response. In contrast, complement activation during the second, extravascular stage of sublethal sepsis via either CRP or mannose-binding lectin (MBL) (Stahl G L, et al., 2003, $Am$ $J$ $Pathol.$ 162: 449-455) can amplify the injury caused initially by oxidative stress and/or histone release. Such amplification acts as a positive feedback leading to a subsequent round of inflammatory activity localized in the tissues rather than in the vasculature, which in turn leads to aberrant responses unique to each tissue or organ, and finally to death in many cases.

Known methods for treating sepsis include antibacterials, antibodies, small molecules and peptides, activated protein C (APC), supportive therapy with oxygen, intravenous fluids, and medications that increase blood pressure. These treatments focus on the initial intravascular stage of sepsis and can rescue patients from sepsis that could otherwise be lethal. However, currently available treatments have not addressed the second stage of sepsis involving an uncontrolled extravascular host recovery response, which can lead to MOF and death. Likewise, complement inhibition has been proposed as a possible therapeutic avenue for treatment of sepsis, but again focusing only on the first stage of the syndrome involving intravascular complement activation in response to pathogen invasion (e.g., Laudes, I. J., et al., 2002, $Am.$ $J.$ $Pathol.$ 160: 1867-1875; Bhole, D & G. L. Stahl, 2003, $Crit$ $Care$ $Med.$ 31: S97-S104; U.S. Patent Publication No. 2007/0274989).

As can be seen from the foregoing discussion, there is a need in the art to identify and develop new methods for the treatment of sepsis, particularly focusing on the extravascular stage oxidative stress-induced events following ischemia reperfusion and histone release. This invention addressed those needs.

SUMMARY OF THE INVENTION

One aspect of the invention features a method for treating sepsis in an individual, which comprises administering a therapeutically effective amount of a complement inhibitor to the individual, wherein the complement inhibitor reduces or prevents sepsis-related extravascular cell, tissue or organ injury in the individual. The complement inhibitor may impart additional benefits in the treatment of sepsis, as described herein. The complement inhibitor can comprise one or more of a C5a inhibitor, a C5aR inhibitor, a C3 inhibitor, a factor D inhibitor, a factor B inhibitor, a C4 inhibitor, a C1q inhibitor, or any combination thereof. In one embodiment, the complement inhibitor is a C3 inhibitor. In particular, the C3 inhibitor is Compstatin, a Compstatin analog, a Compstatin peptidomimetic, a Compstatin derivative, or any combination thereof. The Compstatin or Compstatin analog may comprise any of SEQ ID NO:1, SEQ ID NO.:2, SEQ ID NO:3 or SEQ ID NO:4. The treatment can be administered to any individual identified as needing or benefiting from such treatment, including humans or non-human animals.

In practicing the method, administration of the complement inhibitor can be initiated by, before or after the onset of the extravascular cell, tissue or organ injury in the individual. In one embodiment, administration of the complement inhibitor is initiated immediately upon indication of sepsis. In another embodiment, administration of the complement inhibitor is initiated after sepsis is diagnosed. In particular, administration of the complement inhibitor may be initiated upon observation of persistent or worsening organ failure despite adequate blood pressure. The complement inhibitor can be administered systemically, or it can be administered locally to a tissue or organ.

In one embodiment, the complement inhibitor is administered concurrently with, or sequentially before or after, at least one other sepsis treatment. In particular, the complement inhibitor is administered concurrently with or after administration of one or more agents or regimens for treating initial stages of sepsis. In one embodiment, such agents include one or more of activated protein C (APC), a mutant form of APC, an APC precursor, an APC cofactor, or any combination thereof, and the complement inhibitor is a C3 inhibitor, which can be Compstatin, a Compstatin analog, a Compstatin peptidomimetic, a Compstatin derivative, or any combination thereof.

Another aspect of the invention features a pharmaceutical composition for treating sepsis in an individual, comprising one or more complement inhibitors and at least one anti-sepsis agent, in a pharmaceutically acceptable medium. The complement inhibitor can comprise one or more of a C5a inhibitor, a C5aR inhibitor, a C3 inhibitor, a factor D inhibitor, a factor B inhibitor, a C4 inhibitor, a C1q inhibitor, or any combination thereof. In one embodiment, the complement inhibitor is a C3 inhibitor. In particular, the C3 inhibitor is Compstatin, a Compstatin analog, a Compstatin peptidomimetic, a Compstatin derivative, or any combination thereof. The Compstatin or Compstatin analog may comprise any of SEQ ID NO:1, SEQ ID NO.:2, SEQ ID NO:3 or SEQ ID NO:4. The anti-sepsis agent can be any agent used for the treatment of sepsis. In one embodiment, the anti-sepsis agent comprises one or more of activated protein C (APC), a mutant form of APC, an APC precursor, an APC cofactor, or any combination thereof. The pharmaceutical composition can be formulated for systemic administration or for local administration to a tissue or organ.

Another aspect of the invention features a kit comprising a container or a plurality of containers in a package, and at least one complement inhibitor and at least one other anti-sepsis agent, as well as instructions for use of the complement inhibitor and the anti-sepsis agent for the treatment of sepsis. The complement inhibitor can comprise one or more of a C5a inhibitor, a C5aR inhibitor, a C3 inhibitor, a factor D inhibitor, a factor B inhibitor, a C4 inhibitor, a C1q inhibitor, or any combination thereof. In one embodiment, the complement inhibitor is a C3 inhibitor. In particular, the C3 inhibitor is Compstatin, a Compstatin analog, a Compstatin peptidomimetic, a Compstatin derivative, or any combination thereof. The Compstatin or Compstatin analog may comprise any of SEQ ID NO:1, SEQ ID NO.:2, SEQ ID NO:3 or SEQ ID NO:4. The anti-sepsis agent can be any agent used for the treatment of sepsis. In one embodiment, the anti-sepsis agent comprises one or more of activated protein C (APC), a mutant form of APC, an APC precursor, an APC cofactor, or any combination thereof. The kit can further comprise one or more of: (1) pharmaceutically acceptable media or diluents for the complement inhibitor or the anti-sepsis agent; (2) at least one reagent for detecting markers of an intravascular stage of sepsis; and (3) at least one reagent for detecting markers of an extravascular stage of sepsis.

Other features and advantages of the invention will be understood by reference to the drawings, detailed description and examples that follow.

DETAILED DESCRIPTION OF ILLUSTRATIVE EMBODIMENTS

Figure 1:
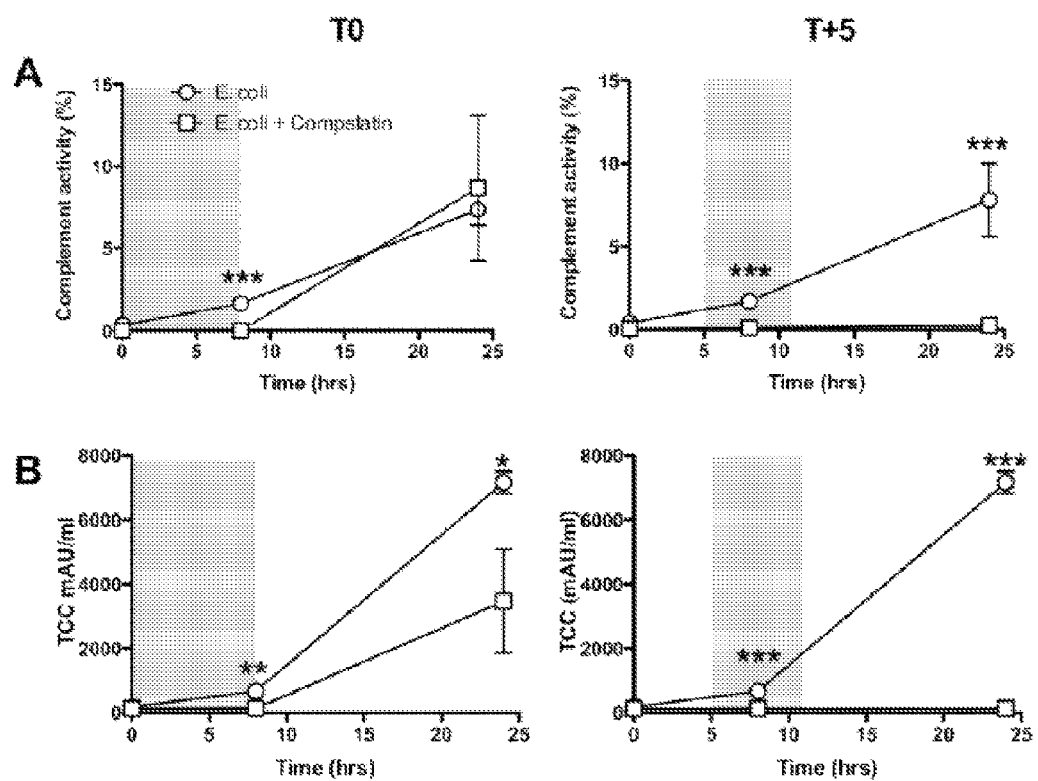
FIG. 1. Complement activity and TCC antigen levels in plasma of baboons treated with a Compstatin analog during the first (T0) and second (T+5) stage of experimental sepsis ($LD_{50}$ model). Data are presented as mean±SEM. Two-tailed Student's t-test:  $p<0.01$; * $p<0.001$.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The singular form of a word includes the plural, and vice versa, unless the context clearly dictates otherwise. Thus, the references "a", "an", and "the" are generally inclusive of the plurals of the respective terms. For example, reference to "a compound" or "a method" includes a plurality of such "compounds" or "methods." Similarly, the words "comprise", "comprises", and "comprising" are to be interpreted inclusively rather than exclusively. Likewise the terms "include", "including" and "or" should all be construed to be inclusive, unless such a construction is clearly prohibited from the context.

The terms "comprising" or "including" are intended to include embodiments encompassed by the terms "consisting essentially of" and "consisting of". Similarly, the term "consisting essentially of" is intended to include embodiments encompassed by the term "consisting of".

Dosages expressed herein are in units per kilogram of body weight (e.g., µg/kg or mg/kg) unless expressed otherwise.

Ranges are used herein in shorthand, to avoid having to list and describe each and every value within the range. Any appropriate value within the range is intended to be included in the present invention, as is the lower terminus and upper terminus, independent of each other.

The term "about" as used herein when referring to a measurable value such as an amount, a temporal duration, and the like, is meant to encompass variations of ±20% or ±10%, in some embodiments ±5%, in some embodiments ±1%, and in some embodiments ±0.1% from the specified value, as such variations are appropriate to practice the disclosed methods or to make and used the disclosed compounds, compositions or articles of manufacture.

The term "antibody" refers to an immunoglobulin molecule that is able to bind specifically to a particular epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

A "complement inhibitor" is a molecule that prevents or reduces activation and/or propagation of the complement cascade that results in the formation of C3a or signaling through the C3a receptor, or C5a or signaling through the C5a receptor. A complement inhibitor can operate on one or more of the complement pathways, i.e., classical, alternative or lectin pathway. A "C3 inhibitor" is a molecule or substance that prevents or reduces the cleavage of C3 into C3a and C3b. A "C5a inhibitor" is a molecule or substance that prevents or reduces the activity of C5a. A "C5aR inhibitor" is a molecule or substance that prevents or reduces the binding of C5a to the C5a receptor. A "C3aR inhibitor" is a molecule or substance that prevents or reduces binding of C3a to the C3a receptor. A "factor D inhibitor" is a molecule or substance that prevents or reduces the activity of Factor D. A "factor B inhibitor" is a molecule or substance that prevents or reduces the activity of factor B. A "C4 inhibitor" is a molecule or substance that prevents or reduces the cleavage of C4 into C4b and C4a. A "C1q inhibitor" is a molecule or substance that prevents or reduces C1q binding to antibody-antigen complexes, virions, infected cells, or other molecules to which C1q binds to initiate complement activation. Any of the complement inhibitors described herein may comprise antibodies or antibody fragments, as would be understood by the person of skill in the art.

Sepsis has been described in detail herein as a multi-stage, multi-factorial and often life threatening clinical syndrome that arises through the innate response to infection. The baboon *E. coli* $LD_{50}$ model of sepsis has given rise to a two-stage or two-compartment model of sepsis that corresponds to clinical observations of human patient populations. The first stage, as described in detail herein, is referred to interchangeably as the "first stage", the "initial stage", the "early stage", the "intravascular stage", and the like. The second stage, as described in detail herein, is referred to interchangeably as the "second stage", the "subsequent stage", the "later stage", the "extravascular stage", and the like.

A "subject", "individual" or "patient" refers to an animal of any species. In various embodiments, the animal is a mammal. In one embodiment, the mammal is a human. In another embodiment, the mammal is a non-human animal.

"Treating" refers to any indicia of success in the treatment or amelioration of the disease or condition. Treating can include, for example, reducing or alleviating the severity of one or more symptoms of the disease or condition, or it can include reducing the frequency with which symptoms of a disease, defect, disorder, or adverse condition, and the like, are experienced by a patient. "Treating" can also refer to reducing or eliminating a condition of a part of the body, such as a cell, tissue or bodily fluid, e.g., blood.

"Preventing" refers to the partial or complete prevention of the disease or condition in an individual or in a population, or in a part of the body, such as a cell, tissue or bodily fluid (e.g., blood). The term "prevention" does not establish a requirement for complete prevention of a disease or condition in the entirety of the treated population of individuals or cells, tissues or fluids of individuals.

The term "treat or prevent" is sometimes used herein to refer to a method that results in some level of treatment or amelioration of the disease or condition, and contemplates a range of results directed to that end, including but not restricted to prevention of the condition entirely.

A "prophylactic" treatment is a treatment administered to a subject (or sample) that does not exhibit signs of a disease or condition, or exhibits only early signs of the disease or condition, for the purpose of decreasing the risk of developing pathology associated with the disease or condition. This term may be used interchangeably with the term "preventing," again with the understanding that such prophylactic treatment or "prevention" does not establish a requirement for complete prevention of a disease in the entirety of the treated population of individuals or tissues, cells or bodily fluids.

As used herein, a "therapeutically effective amount" or simply an "effective amount" is the amount of a composition sufficient to provide a beneficial effect to the individual to whom the composition is administered, or who is otherwise treated using a method involving the composition.

Description

The present invention springs in part from the inventors' demonstration, using a baboon model of *E. coli* sepsis, that inhibition of complement activation effectively attenuates inflammatory and hemostatic processes, restores systemic blood pressure and improves organ function during severe sepsis.

Complement activation is an important innate immune host defense response, supporting leukocyte recruitment to the site of infection, phagocytosis and killing of the bacteria. Complement activation can also be triggered when blood is exposed to damaged vascular tissues, e.g., following oxidative stress caused by IR occurring as an aftermath of the inflammatory response to sepsis, or as a result of histones released into the blood. The inventors have demonstrated that this later, extravascular stage of sepsis represents a valuable therapeutic window for the use of complement inhibitors to prevent tissue damage and organ failure.

The *E. coli* intravenous infusion model described herein exhibits two distinct stages of disease progression, which correspond to clinical observations in human patient populations. The first stage is highly coagulopathic and is driven by the inflammatory response to the infused bacteria. The inflammatory mediators upregulate tissue factor (TF) on circulating monocytes and tissue macrophages, which leads to massive intravascular fibrin deposition (disseminated intravascular coagulation, DIC) and hypo-perfusion of vital organs. Under ischemic conditions caused by the initial stage of sepsis, hypoxia-inducible genes are upregulated, and reduced oxygen supply leads to increased neutrophil adherence, transmigration, oxidative burst and enhanced production of reactive oxygen and nitrogen species. These events fuel the second stage by promoting cell and tissue injury and predisposing to organ dysfunction, ultimately leading to organ failure and death in about 50% of subjects. In addition, as part of the normal mechanism for clearing bacteria from the circulation, neutrophils generate extracellular antimicrobial responses known as neutrophil extracellular traps (NETs), which capture the bacteria. NETS contain histones, among other elements, which can be released into the circulation. These circulating histones are cytotoxic and, as discussed in Example 8, are associated with the generation of complement activation products.

In the baboon model described herein, histopathological analysis of organs showed evidence of aberrant tissue repair in the lung, thrombotic angiopathic lesions in the kidney and cell death (apoptosis/necrosis) in kidneys, adrenals and lymphoid organs. It was previously shown that complement activation peaks during both stages of sepsis in baboons, but it plays distinct pathophysiological roles in each stage (Taylor, F B, Jr. et al. 2006, *Adv Exp Med Biol.* 586: 203-216). The TCC plasma level during the second stage, when the bacteremia is close to zero, exceeds the activation seen during the highly bacteremic first stage and coincides with the rise of C-reactive protein (CRP) levels. Complement activation and deposition on endothelium during this stage can result in a loss of vascular homeostasis, triggering the second round of procoagulant and proinflammatory events observed during the later stages of sepsis.

As described in greater detail in the examples, inhibition of complement activation by a potent inhibitor of C3 activation, a key event common to all three complement activation pathways, was shown to have organ-protective effects in both early and late treatment regimens. The protective effect of the complement inhibitor when administered during the, sterile second stage indicates that complement activation during this time-frame contributes to disease progression towards organ failure and death. Thus, in accordance with the present invention, blocking of complement activation during the second stage is advantageous. In addition, blocking of complement at the early phase virtually completely abolished the fall in systemic blood pressure, indicating that complement activation is responsible for one of the most important physiological disturbances during early sepsis. Thus, inhibition of complement activation at the early stage also should provide some benefit.

The fact that late intervention of complement activation (5 hrs post-challenge) still provides organ protection is important, as most septic patients receive medical attention after the debut of the disease. These findings are particularly notable as few, if any, therapeutic agents for sepsis show organ protective effects when administered so late. For instance, a currently used therapeutic, activated protein C (APC) has therapeutic efficiency in baboons only when administered 1-2 hours post-challenge.

Accordingly, one aspect of the present invention features a method for treating sepsis in an individual, comprising administering a therapeutically effective amount of a complement inhibitor to the individual, wherein the complement inhibitor reduces or prevents extravascular cell, tissue and organ injury in the individual. The timing of such administration may vary, keeping in mind that the therapeutic effect of complement inhibitor administration is observed mainly in the second, extravascular stage of sepsis, which can overlap the initial intravascular stage. Accordingly, administration of complement inhibitors may be initiated as soon as sepsis is diagnosed, and indeed is shown to have a beneficial effect on blood pressure in the early stage, in the baboon $LD_{50}$ model. Administration of complement inhibitors also may be initiated later, i.e., after the infection that caused the sepsis has been controlled (naturally or due to antibiotic treatment), or after the intravascular coagulopathic events have peaked. In either approach, CI is continued through the subsequent extravascular stage, to attenuate complement-mediated damage to cells, tissues and organs.

Thus, in one embodiment, complement inhibitor (CI) therapy can be initiated as soon as sepsis is diagnosed. In this embodiment, if such diagnosis is made while the sepsis-causing infection is active, CI therapy may be administered together with antibiotics or other antimicrobial therapy. CI therapy may continue throughout the initial intravascular stage and should continue throughout the subsequent extravascular stage. In another embodiment, CI therapy is timed to target the second stage more precisely. In this embodiment, the CI therapy may be initiated at some time after initial diagnosis of sepsis, when onset of second stage events is detected. In this embodiment, the CI therapy also is continued through the second stage.

For purposes of timing CI therapy, the stages of sepsis can be determined in a variety of ways well known to physicians, medicinal chemists or others of skill in the art. For example, at one level, the second stage of sepsis may be inferred for any patient who survives the first 48 hours of sepsis. Alternatively or additionally, the second stage of sepsis may be inferred for a patient exhibiting persistent or worsening of organ failure despite an adequate blood pressure (either unaided or supported by fluids and/or pressors). In either instance the physician may determine that CI therapy is warranted, assuming the therapy has not been initiated at the initial diagnosis of sepsis. Another clinical parameter to consider is the trending direction of platelet count. Typically, the onset of sepsis is associated with a decline in circulating platelets. Failure of the platelet count to increase after a period of time (e.g., about 48 hours) indicates a poor prognosis for the patient, which could be improved by CI therapy.

Alternatively or additionally, other biomarkers may be utilized to identify the stages of sepsis. For instance, in addition to clinical indications (heart rate, respiration, blood pressure, urine output), the initial stage may be characterized by elevation of coagulation-related molecules in the blood or a decrease in molecules consumed during coagulation (e.g., fibrinogen), or by coagulation tests, e.g., activated partial thromboplastin time (aPTT), prothrombin time (PT), fibrin degradation products (FDP) or thrombin-antithrombin complexes (TAT). The second stage may be characterized, for instance, via biochemical tests for organ function, e.g., lactate, creatinine, lactate dehydrogenase (LDH), alkaline aminotransferase (ALT), aspartate transaminase (AST) or alkaline phosphatase (ALP). The presence or amount of histones or histone-DNA complexes (nucleosomes) is also an indicator of kidney or adrenal damage that can occur in the second stage of sepsis.

A positive outcome or endpoint of the CI treatment may be determined by one or more of the following clinical or histological indications: (1) reduction in blood and/or tissue biomarkers of complement activation; (2) reduced leucopenia and/or thrombocytopenia; (3) lowered accumulation of macrophages and platelets in organs; (4) decreased coagulopathic response measured by downregulation of tissue factor and/or PAI-1, (5) diminished global blood coagulation-activation markers (fibrin-degradation products, APTT) and elevated fibrinogen; (6) preservation of endothelial anticoagulant properties; (7) improvement in cardiac function and/or the biochemical markers of kidney and liver damage; and/or (8) histological analysis of organs showing decreased microvascular thrombosis, improved vascular barrier function, and/or less leukocyte infiltration and cell death.

The above listed indicators are representative of the types of indicators that can be used by the clinician to determine when to begin and/or end CI therapy for sepsis, in accordance with the present invention. The skilled artisan will appreciate numerous other indicators, and combinations of indicators that can be utilized for this purpose.

As mentioned above, a "complement inhibitor" is a molecule that prevents or reduces activation and/or propagation of the complement cascade that results in the formation of C3a or signaling through the C3a receptor, also referred to herein as "C3a activity," or formation of C5a or signaling through the C5a receptor, also referred to herein as "C5a activity". A complement inhibitor can operate on one or more of the complement pathways, i.e., classical, alternative or lectin pathway.

Any inhibitor of C3a or C5a formation or activity may be used in the method of the invention. In one embodiment, a C3 inhibitor is used. Preferably, the C3 inhibitor is Compstatin or a Compstatin analog, derivative, aptamer or peptidomimetic. Compstatin is a small molecular weight cyclic peptide having the sequence Ile-Cys-Val-Val-Gln-Asp-Trp-Gly-His-His-Arg-Cys-Thr (SEQ ID NO. 1). Examples of Compstatin analogs, derivatives and peptidomimetics are described in the art. See, for instance, U.S. Pat. No. 6,319,897, U.S. Pat. No. 7,888,323, WO/1999/013899, WO/2004/026328 and WO/2010/127336.

An exemplary Compstatin analog comprises a peptide having a sequence: Xaa1-Cys-Val-Xaa2-Gln-Asp-Trp-Gly-Xaa3-His-Arg-Cys-Xaa4 (SEQ ID NO. 2); wherein:

Xaa1 is Ile, Val, Leu, Ac-Ile, Ac-Val, Ac-Leu or a dipeptide comprising Gly-Ile;

Xaa2 is Trp or a peptidic or non-peptidic analog of Trp;
Xaa3 is His, Ala, Phe or Trp;
Xaa4 is L-Thr, D-Thr, Ile, Val, Gly, or a tripeptide comprising Thr-Ala-Asn, wherein a carboxy terminal —OH of any of the L-Thr, D-Thr, Ile, Val, Gly or Asn optionally is replaced by —NH$_2$; and the two Cys residues are joined by a disulfide bond. Xaa1 may be acetylated, for instance, Ac-Ile. Xaa2 may be a Trp analog comprising a substituted or unsubstituted aromatic ring component. Non-limiting examples include 2-naphthylalanine, 1-naphthylalanine, 2-indanylglycine carboxylic acid, dihydrotryptophan or benzoylphenylalanine.

Another exemplary Compstatin analog comprises a peptide having a sequence: Xaa1-Cys-Val-Xaa2-Gln-Asp-Xaa3-Gly-Xaa4-His-Arg-Cys-Xaa5 (SEQ ID NO. 3); wherein:
Xaa1 is Ile, Val, Leu, Ac-Ile, Ac-Val, Ac-Leu or a dipeptide comprising Gly-Ile;
Xaa2 is Trp or an analog of Trp, wherein the analog of Trp has increased hydrophobic character as compared with Trp, with the proviso that, if Xaa3 is Trp, Xaa2 is the analog of Trp;
Xaa3 is Trp or an analog of Trp comprising a chemical modification to its indole ring wherein the chemical modification increases the hydrogen bond potential of the indole ring;
Xaa4 is His, Ala, Phe or Trp;
Xaa5 is L-Thr, D-Thr, Ile, Val, Gly, a dipeptide comprising Thr-Asn or Thr-Ala, or a tripeptide comprising Thr-Ala-Asn, wherein a carboxy terminal —OH of any of the L-Thr, D-Thr, Ile, Val, Gly or Asn optionally is replaced by —NH$_2$; and the two Cys residues are joined by a disulfide bond. The analog of Trp of Xaa2 may be a halogenated tryptophan, such as 5-fluoro-1-tryptophan or 6-fluoro-1-tryptophan. The Trp analog at Xaa2 may comprise a lower alkoxy or lower alkyl substituent at the 5 position, e.g., 5-methoxytryptophan or 5-methyltryptophan. In other embodiments, the Trp analog at Xaa 2 comprises a lower alkyl or a lower alkenoyl substituent at the 1 position, with exemplary embodiments comprising 1-methyltryptophan or 1-formyltryptophan. In other embodiments, the analog of Trp of Xaa3 is a halogenated tryptophan such as 5-fluoro-1-tryptophan or 6-fluoro-1-tryptophan.

Another set of exemplary Compstatin analogs features Compstatin or any of the foregoing analogs, in which Gly at position 8 is modified to constrain the backbone conformation at that location. In one embodiment, the backbone is constrained by replacing the Gly at position 8 (Gly8) with Nα-methyl Gly.

Other C3 inhibitors include vaccinia virus complement control protein (VCP) and antibodies that specifically bind C3 and prevent its cleavage.

Inhibition of C5a formation or activity may be accomplished in a variety of ways. For instance, C5a activity may be inhibited directly by preventing or significantly reducing the binding of C5a to its receptor, C5aR. A number of C5aR inhibitors are known in the art. Acetyl-Phe-[Orn-Pro-D-cyclohexylalanine-Trp-Arg] (AcF[OPdChaWR]; PMX-53; Peptech) is a small cyclic hexapeptide that is a C5aR antagonist and is exemplified herein. Analogs of PMX-53 (e.g., PMX-201 and PMX-205) that also function as C5aR antagonists are also available (see for instance Proctor et al., 2006, *Adv Exp Med Biol.* 586:329-45 and U.S. Pat. Pub. No. 20060217530). Neutrazumab (G2 Therapies) binds to C5aR, thereby inhibiting binding of C5a to C5aR. Neutrazumab (G2 Therapies) binds to extracellular loops of C5aR and thereby inhibits the binding of C5a to C5aR. TNX-558 (Tanox) is an antibody that neutralized C5a by binding to C5a.

C5a activity may also be inhibited by reducing or preventing the formation of C5a. Thus, inhibition of any step in the complement cascade that contributes to the downstream formation of C5a is expected to be effective in practicing the invention. Formation of C5a may be inhibited directly by inhibiting the cleavage of C5 by C5-convertase. Eculizumab (Alexion Pharmaceuticals, Cheshire, Conn.) is an anti-C5 antibody that binds to C5 and prevents its cleavage into C5a and C5b. Pexelizumab, an scFv fragment of Eculizumab, has the same activity. Similarly, ARC 1905 (Archemix), an anti-C5 aptamer, binds to and inhibits cleavage of C5, inhibiting the generation of C5b and C5a.

In other embodiments, formation of C3a or C5a is reduced or prevented through the use of an inhibitor of complement activation prior C3 cleavage, e.g., in the classical or lectin pathways of complement activation. Non-limiting examples of such inhibitors include, but are not limited to: (1) factor D inhibitors such as diisopropyl fluorophosphates and TNX-234 (Tanox), (2) factor B inhibitors such as the anti-B antibody TA106 (Taligen Therapeutics), (3) C4 inhibitors (e.g., anti-C4 antibodies) and (4) C1q inhibitors (e.g., anti-C1q antibodies).

Antibodies useful in the present invention, such as antibodies that specifically bind to either C4, C3 or C5 and prevent cleavage, or antibodies that specifically bind to factor D, factor B, C1q, or the C3a or C5a receptor, can be made by the skilled artisan using methods known in the art. See, for instance, Harlow, et al., 1988, In: Antibodies, A Laboratory Manual, Cold Spring Harbor, N.Y.), Tuszynski et al., 1988, *Blood,* 72:109-115), U.S. patent publication 2003/0224490, U.S. Pat. No. 6,180,370 to Queen et al., Wright et al., 1992, *Critical Rev. Immunol.* 12(3,4):125-168), Gu et al., 1997, *Thrombosis and Haemostasis* 77(4):755-759, and Burton et al., 1994, *Adv. Immunol.* 57:191-280. Anti-C3 and anti-C5 antibodies are also commercially available.

The invention encompasses the use of pharmaceutical compositions comprising a complement inhibitor to practice the methods of the invention. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

Thus, in addition to the methods described above, other aspects of the invention features pharmaceutical compositions for the treatment of sepsis, comprising at least one complement inhibitor and, in certain embodiments, one or more other anti-sepsis agents as described more fully below.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-does unit.

As used herein, the term "pharmaceutically acceptable carrier" means a chemical composition with which a complement inhibitor may be combined and which, following the combination, can be used to administer the complement inhibitor to a mammal.

As used herein, the term "physiologically acceptable" or "pharmaceutically acceptable" ester or salt means an ester or salt form of the active ingredient which is compatible with any other ingredients of the pharmaceutical composition, which is not deleterious to the subject to which the composition is to be administered.

The concentration of active ingredient suitable for use in the present invention will vary depending upon any number of factors, including but not limited to, the type of patient, the type or severity of the condition, the age of the patient and the route of administration. Preferably, the dosage of the compound will vary from about 10 micrograms to about 10 grams per kilogram of body weight of the patient. More preferably, the dosage will vary from about 100 micrograms to about 1 gram per kilogram of body weight of the patient. More preferably, and as exemplified herein for the C3-inhibiting Compstatin analog, the dosage will vary from about 1 milligram to about 100 milligrams per kilogram body weigh. Higher concentrations are particularly useful when administered as an initial bolus following the onset of sepsis as discussed above. The initial bolus can be followed by continuous infusion of a lower concentration of complement inhibitor, e.g., 10-100 micrograms per kilogram body weight per minute.

A single complement inhibitor may be administered, or two or more different complement inhibitors may be administered in the practice of the method of the invention. In one embodiment of the invention, the method comprises administration of only a complement inhibitor or a combination of complement inhibitors.

As discussed above, blocking the harmful effects of complement activation products during the second (organ failure) stage of severe sepsis provides an important therapeutic strategy, heretofore not available. Since the pathophysiological events of this stage occur after the infection is cleared or controlled, blockade of complement activity should not interfere with the beneficial effects of complement activation. The data set forth herein show that complement inhibition, although efficiently attenuating hypotension when given early, is still effective even when given during the second stage of progressive organ failure. Thus, complement inhibition during the second stage may be utilized in combination therapies with other agents or regimens used to treat sepsis. Such agents are sometimes referred to collectively herein as "anti-sepsis agents," and include, but are not limited to, antibacterials, antibodies, small molecules and peptides, supportive therapy with oxygen, intravenous fluids, and medications that increase blood pressure and particularly may include inhibitors of upstream inducers of inflammation, such as anti-CD14 antibodies or APC, the latter of which is effective during the early shock/DIC response to severe sepsis, and which has been shown also to target and cleave histone proteins, thereby offering an additional therapeutic effect in the second stage of sepsis.

A particular embodiment of the invention features a combination therapy for the treatment of sepsis, comprising a complement inhibitor and one or more of APC (native or mutants), Protein C concentrate or soluble thrombomodulin. APC is commercially available for therapeutic use in humans as XIGRIS® (drotrecogin alfa (activated), a recombinant form of human APC, Eli Lilly) and is administered via infusion immediately upon diagnosis of severe sepsis and for 96 hours thereafter. Protein C concentrate is available for therapeutic use in humans as CEPROTIN® (Baxter Healthcare Corporation) and is the proenzyme form of APC. Thrombomodulin is a key cofactor in the APC generation pathway. Recombinant soluble thrombomodulin (sTM) is produced by Artisan Pharma, Inc. (under the trade-name ART-123). Thus, in one embodiment, a combined therapy consisting of APC or APC precursors or cofactors such as PC or sTM (referred to collectively as "APC") and a complement inhibitor (CI) can comprise (a) initiating administration of both drugs immediately upon diagnosis of severe sepsis, (b) continuing the APC regimen for the prescribed time period and (c) continuing the CI therapy for the same time period or, optionally, for a different time period, such as until an endpoint to the extravascular stage of sepsis is indicated, as described above. In another embodiment, administration of the APC can precede administration of the CI, as described above in the section discussing the timing of CI therapy. In yet another embodiment, APC therapy may be extended for more than 96 hours, should a clinical benefit resulting from, e.g., its activity against histones during the second stage of sepsis, be established.

A particular embodiment features a combination therapy comprising administration of (1) APC (native or mutants) or Protein C concentrate or soluble thrombomodulin; and (2) Compstatin or a Compstatin analog, derivative, aptamer or peptidomimetic, as described above. More particularly, this embodiment features a combination therapy comprising administration of APC and a Compstatin analog.

The combination therapy comprising CI, particularly Compstatin and analogs, and APC should be particularly suitable for treatment of severe sepsis, where APC is currently approved for use. The reason for this is that, while complement inhibition in the initial stages of less severe sepsis (e.g., the $LD_{50}$ model in baboons) has been shown to improve blood pressure, it appears to be ineffective in rescuing animals from the first stage of severe sepsis (e.g., as observed in the baboon $LD_{100}$ model; see Example 7). Thus, the combination therapy, with APC therapy enabling the patient to survive the first stage of severe sepsis, and CI reducing tissue and organ damage during the later stages, should be advantageous. The advantages are even more noteworthy when the additional therapeutic effects of CI and APC are considered, i.e., CI-mediated improvement in blood pressure, and APC-mediated cleavage of histone proteins, which contribute to extravascular complement activation.

Pharmaceutical compositions that are useful in the aforementioned embodiments may be administered systemically in oral solid formulations, parenteral, intravenous, ophthalmic, suppository, aerosol, topical or other similar formulations. Such pharmaceutical compositions may contain pharmaceutically acceptable carriers and other ingredients known to enhance and facilitate drug administration. Other formulations, such as nanoparticles, liposomes, resealed erythrocytes, and immunologically based systems also may be used to administer a complement inhibitor according to the methods of the invention.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Suitable formulations include, for example, those that comprise the active ingredient in microcrystalline form, in a liposomal preparation, in microbubbles for ultrasound-released delivery or as a component of a biodegradable polymer system. Compositions for sustained release or implantation may comprise pharmaceutically acceptable polymeric or hydrophobic materials sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibacterial agents; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The pharmaceutical compositions comprising complement inhibitors and/or other active agents or additional ingredients, can be conveniently packaged together in kits. Such kits comprise at least the complement inhibitor and instructions for its use in treating sepsis. Such kits may also comprise the complement inhibitor and another anti-sepsis agent, along with instructions for their use in treating sepsis. The kits may also comprise one or more of the diluents, excipients, carriers and other ingredients referred to above. They may also comprise reagents and other components for diagnosing or detecting the stages of sepsis, such as reagents to detect biomarkers of the intravascular and/or extravascular stages, as described herein.

The following examples are provided to describe the invention in greater detail. They are intended to illustrate, not to limit, the invention.

Example 1

Materials and Methods

This example sets forth the materials and experimental methods used to generate the results described in Examples 2-6.

Reagents.

Antibodies and suppliers used were as follows: rabbit anti-human neutrophil elastase (Calbiochem, San Diego, Calif.); monoclonal antibodies (mAb) anti-MHC-II, anti-CD68, anti-thrombomodulin (TM), anti-GPIIIa and rabbit polyclonal anti-human myeloperoxidase (DakoCytomation, Carpinteria, Calif.); mAb anti-tissue factor (TF, clone TF9-10H10; gift from Dr. Jim Morrissey); rabbit anti-TFPI IgG (raised and characterized in-house); mAb anti C3a (clone 4DS17.3, gift from Dr. Bo Nilsson); mAb anti-C3b (Clone C3-28, gift from Dr. Diana Wouters); mAb anti-C5b9 (clone aE11, Diatec, Oslo, Norway); mAb anti-MBL (AbD Serotec, Raleigh, N.C.); mAb anti-CD55 (Abcam Inc., Cambridge, Mass.); mAb anti-CD59 (BD Biosciences Inc., San Diego, Calif.); mAb anti-PAI1 7F5, (gift from Dr. P. DeClerck). FITC, Cy3 or Cy5 conjugated donkey anti-mouse or anti-rabbit secondary antibodies were from Jackson ImmunoResearch Laboratories (West Grove, Pa.).

The Compstatin analog (Ac-I[CVW(Me)QDWGAHRCT]I-NH$_2$) (SEQ ID NO:4) was synthesized as described (Katragadda M, et al., 2006, *J Med Chem.* 49: 4616-4622).

The primers were synthesized by Integrated DNA Technologies, San Diego, Calif.

Live *E. coli* organisms (serotype B7-086a:K61; American Type Culture Collection, Rockville, Md.), stored in the lyophilized state at 4° C. after growth in tryptic soybean agar, were reconstituted and used. To eliminate differences due to *E. coli* strain variations, all animals were infused with *E. coli* from this single isolate.

Experimental Procedures

*Papio cyanocephalus* baboons were held for 30 days at an animal facility. Only healthy tuberculosis free animals with hemoglobin greater than 10 g/dL and white blood cell (WBC) count less than 12,000 were included in the study. Animals were infused with $1 \times 10^9$ live *E. coli* ($LD_{50}$ dose) as described (Taylor F B, Jr., et al., 2000, *Blood* 95: 1680-1686). The time point at which the infusion was started is further indicated as T-0, a time point of n hours thereafter referred to as T+n hours. The Compstatin analog was administered as a 10-mg/kg iv. bolus followed by 60 µg/kg/min continuous infusion. Three experimental *E. coli* groups were studied: (i) *E. coli* challenge only (n=4); (ii) *E. coli* plus Compstatin analog treatment from T0 to T+8 (n=4; prevention regimen); (iii) *E. coli* plus Compstatin analog from T+5 to T+11 (n=4; rescue regimen). In one additional experiment (n=1), aimed to test the inhibitory properties of the Compstatin analog on the generation of complement activation products, administration of the Compstatin analog was delayed until T+11.

The control group comprising three animals received saline infusion only. Physiological data [temperature, mean systemic arterial pressure (MSAP), heart and respiration rate] and blood samples were collected at T0, +1, 2, 4, 6, 8 12 and 24 hrs as described (Taylor et al., 2000, supra). The following assays were performed during the time-course of the experiments: complete blood cell count, including hematocrit, platelets and WBC, coagulation tests (fibrinogen, APTT, PT, FDP, TAT) and organ function biochemical tests, including lactate, creatinine, lactate dehydrogenase (LDH), alanine aminotransferase (ALT), aspartate transaminase (AST) and alkaline phosphatase (ALP). Animals were sacrificed at T+24 and tissue specimens were removed from the lungs, kidney, adrenals, heart and spleen, snap frozen in liquid nitrogen and stored at −80° C. or fixed for microscopy (Tang H, et al., 2007, *Am J Pathol.* 171: 1066-1077).

The complement activation products C3a, C3b, and TCC and complement activity were measured in accordance with known methods. Cyokines were measured using a multiplex assay (Non-human primate cytokine/chemokine assay, Bio-Rad Laboratories, Hercules, Calif.), which can detect 23 different interleukins, chemokiens and cytokines. The assay was performed according to the instructions from the manufacturer.

Morphological Analysis.

For immunofluorescence, tissues were fixed in 4% paraformaldehyde, washed with phosphate-buffered saline containing 15% sucrose, embedded in OCT, snap-frozen, and stored at −80° C.

Immunolabeling for PAI-1, TF, TFPI, TM, MBL, C5b9, CD55, CD59 and cell markers (MHC-II and CD68 for dendritic cells and macrophages, myeloperoxidase or elastase for neutrophils, gpIIIa for platelets, CD31 for endothelial cells) was performed. Briefly, cryosections (approximately 10 μm thick) were incubated with the primary antibodies (see "Reagents") overnight at 4° C.; followed by appropriate detection antibodies coupled to FITC, Cy3 or Cy5 fluorophores and mounted with VectaShield® hardset mounting medium (Vector Labs, Burlingame, Calif.) supplemented with ToPro3 (Invitrogen, Carlsbad, Calif.) as nuclear counterstaining.

As negative control for polyclonal antibody staining, the primary antibodies were replaced with equivalent amounts of rabbit non-immune serum. mAb anti-digoxigenin (IgG1; Roche Diagnostics, Indianapolis, Ind.), a hapten antigen that occurs only in plants, was used as isotype-matched control for mAb staining.

The samples were analyzed by confocal laser scanning microscopy using a Nikon C1 scanning head mounted on a Nikon ECLIPSE 2000U inverted microscope, equipped with either a ×20 plan achromat objective (NA 0.46, dry) or a ×60 apochromat objective (NA 1.2, water immersion). The measurement of fluorescence intensity was performed according to published methods. In brief, 10 to 15 images (12-bit, 4095 gray levels/pixel) were collected for each experimental condition, and the mean fluorescence intensity (MFI) of the whole image or 15-20 regions-of-interest (ROI) per image was integrated using the EZ-C1 software (Nikon). Image collection parameters (neutral density filters, pinhole, and detector gains) were kept constant during image acquisition, to make reliable comparisons between specimens. Histopathological analysis was done on paraffin sections stained with phosphotungstic acid or hematoxylin eosin by an experienced veterinary pathologist who was blinded for the experimental conditions.

Quantitative Reverse Transcriptase-Polymerase Chain Reaction (qRT-PCR)-Based Gene Expression Analysis.

Real-time qRT-PCR was used to determine the relative amount of TF, TFPI-α, TM, PAI-1, CD55, CD59 and β-actin mRNA in the baboons' lung or liver. Primers were designed using Primer Express software (Applied Biosystems, Foster City, Calif.).

Total RNA was extracted using TRIzol (Invitrogen), further purified with the Qiagen DNeasy Tissue kit (Qiagen, Valencia, Calif.) and the contaminant genomic DNA was removed with a Qiagen on-column DNase digestion kit. For each sample, 5 μg of total RNA was reverse-transcribed using the SuperScript III first-strand synthesis system for RT-PCR (Invitrogen) with random hexamer primers. Real-time PCR was performed in duplicate with 2 μl of the 50-μl RT reaction products using iTaq SYBR Green Supermix with ROX kit (Bio-Rad, Hercules, Calif.) in an ABI Prism 7000 sequence detection system (Applied Biosystems, Foster City, Calif.). Relative quantification of gene expression was estimated using ΔΔ CT method, following the manufacturer's protocol. The relative expression of target genes was normalized with β-actin mRNA level as housekeeping gene or 18S rRNA.

Statistical Analysis.

For statistical analyses, Prism (GraphPad Software, Inc., San Diego, Calif.) was used. Values are given as mean±SEM. The differences between *E. coli*-challenged groups, with/without Compstatin analog treatment, were compared by a two-tailed, unpaired t test or one-way analysis of variance (ANOVA), followed by single comparison with the *E. coli* challenged group by using Dunnett test. Differences were considered as significant when $p<0.05$. All assays were performed at least in duplicate.

Example 2

Effect of Complement Inhibition on Markers of Complement Activation

Compstatin is a 13-residue cyclic, non-immunogenic peptide that specifically binds to primate C3, hindering the interaction of C3 with the C3 convertase complex (Janssen B J, et al., 2007, *J Biol Chem.* 282: 29241-29247) and thus preventing the proteolytic activation of C3. Compstatin inhibits baboon and human complement at approximately equimolar concentrations (Sahu A, et al., 2003, *Molec. Immunol.* 39: 557-566).

Infusion with the Compstatin analog described above rapidly inhibited C3a and C3b generation in septic baboons. Complement activity and plasma TCC levels were measured to evaluate the effect of Compstatin analog treatment on *E. coli*-induced complement activation. Both preventive (T0 to T+8) and rescue (T+5 to T+11) Compstatin analog treatments inhibited plasma complement activity (FIG. 1A) and plasma TCC levels, the rescue regimen averting the late rise observed in the prevention group (FIG. 1B).

Figure 2:
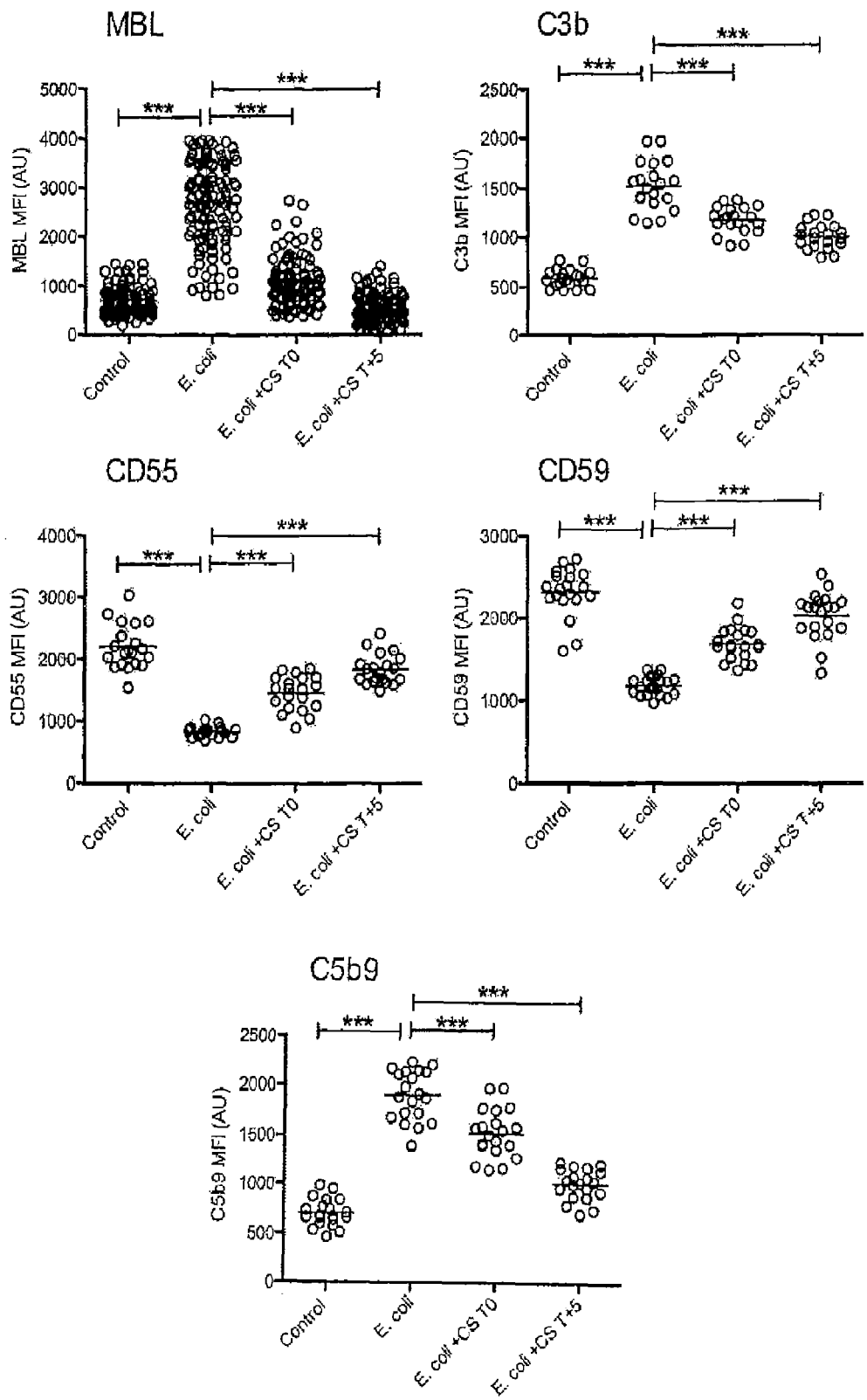
FIG. 2. Quantitative analysis of fluorescence intensity in kidneys stained for several complement pathway proteins in baboons treated with a Compstatin analog during the first (T0) and second (T+5) stage of experimental sepsis ($LD_{50}$ model). Scatter-plot representation of mean fluorescence intensity (MFT) of images collected (not shown) for mannose binding lectin (MBL) C3b, TCC (C5b9), CD55 and CD59 in healthy controls, septic baboons (*E. coli*), and septic baboons treated with a Compstatin analog (CS) during the first (*E. coli*+CS T0) or the second (*E. coli*+CS T+5) stage. Scatter-plot data are shown as mean±SEM. One-way ANOVA with Dunnett's multi-comparison test: *** $p<0.0001$, compared with the *E. coli* group.

Immunofluorescence staining of kidney cryosections followed by quantitative confocal microscopy analysis showed that *E. coli* sepsis induced significant levels of C3b and C5b9 staining in peritubular capillaries and glomeruli, and MBL in peritubular capillaries (FIG. 2). Compstatin analog treatment significantly inhibited MBL, C3b and C5b9 deposition in the kidney, suggesting decreased endothelial injury and IR induced nephrotoxicity. Moreover, Compstatin analog treatment protected against shedding of CD55 and CD59 from the endothelial surface (FIG. 2) without significantly affecting the mRNA expression of these proteins (not shown). CD55 and CD59 are major negative regulators of complement function, which prevent uncontrolled activation of complement and widespread tissue damage.

Example 3

Effects of Complement Inhibition on Hematological Parameters

Figure 3:
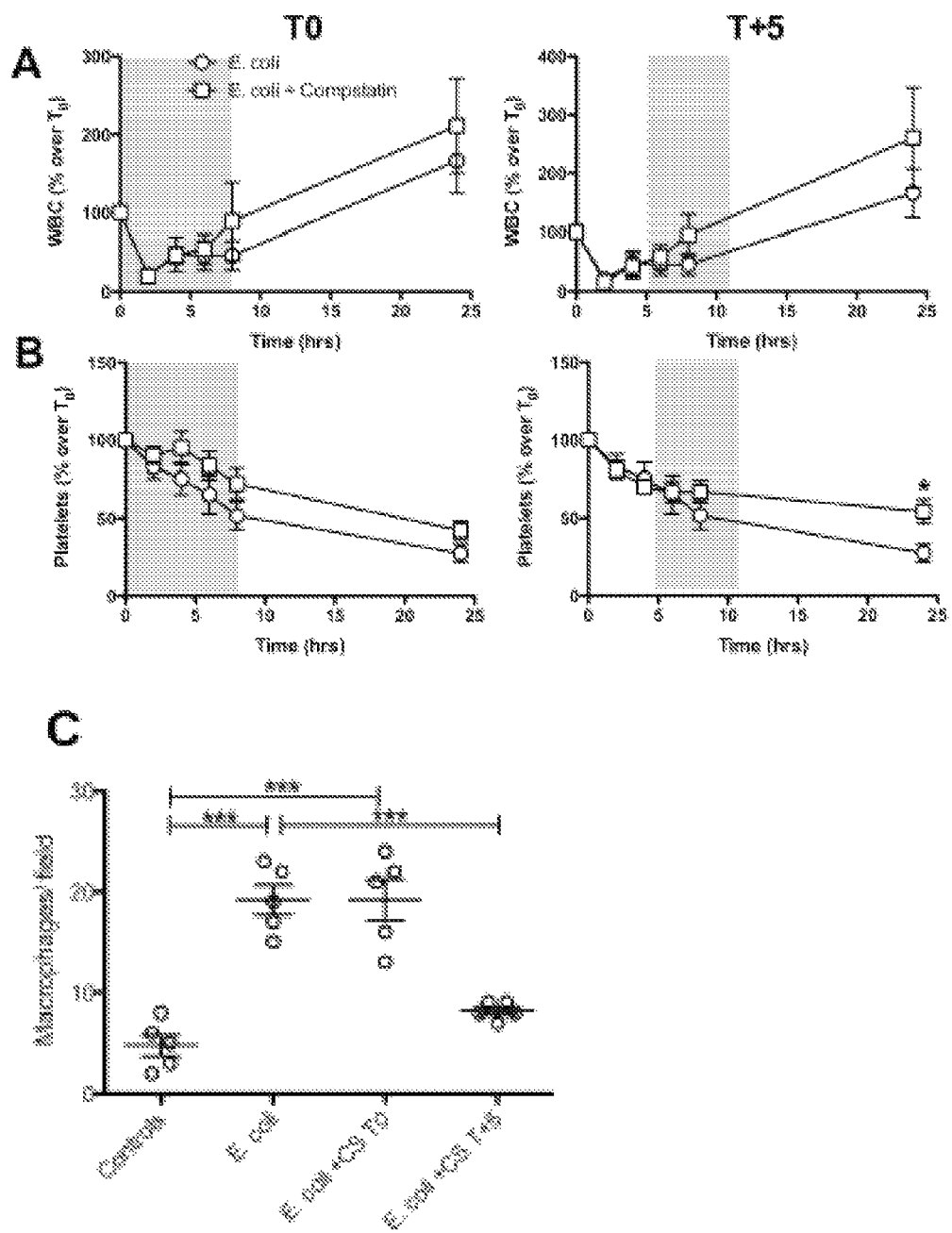
FIG. 3. Effect of Compstatin analog treatment on blood cells in baboons treated with a Compstatin analog during the first (T0) and second (T+5) stage of experimental sepsis ($LD_{50}$ model). A-B. Time-course of WBC (A) and platelet (B) counts in the blood of baboons treated with a Compstatin analog during the first (T0) and second (T+5) stage of experimental sepsis. Data are presented as mean±SEM. Two-tailed Student's t-test: * $p<0.05$. C: Quantization of CD68 positive macrophages in the lung of healthy controls, septic baboons (*E. coli*), and septic baboons treated with the Compstatin analog (CS) during the first (*E. coli*+CS T0) or the second (*E. coli*+CS T+5) stage. Scatter-plot data are shown as mean±SEM; One-way ANOVA with Dunnett's multi-comparison test: *** $p<0.0001$, compared with *E. coli* group.

The influence of Compstatin analog treatment on hematological responses to *E. coli* challenge is shown in FIG. 3. *E.*

*coli* infusion induced a rapid fall in leukocyte count during the first hour and a steady decline of platelets. Compstatin analog treatment led to a faster WBC recovery (FIG. 3A) and lower plasma platelet consumption (FIG. 3B) in both the prevention and rescue regimens. The higher WBC and platelet counts in blood correlated with lower accumulation of macrophages (FIG. 3C) and platelets in the lung (FIG. 3D) and on the surface of the large vessels (FIG. 3E), as well as with decreased C5b9 deposition on aggregated platelets detected in these organs (FIG. 3D-E).

Example 4

Effects of Complement Inhibition on Coagulation Biomarkers

Figure 4:
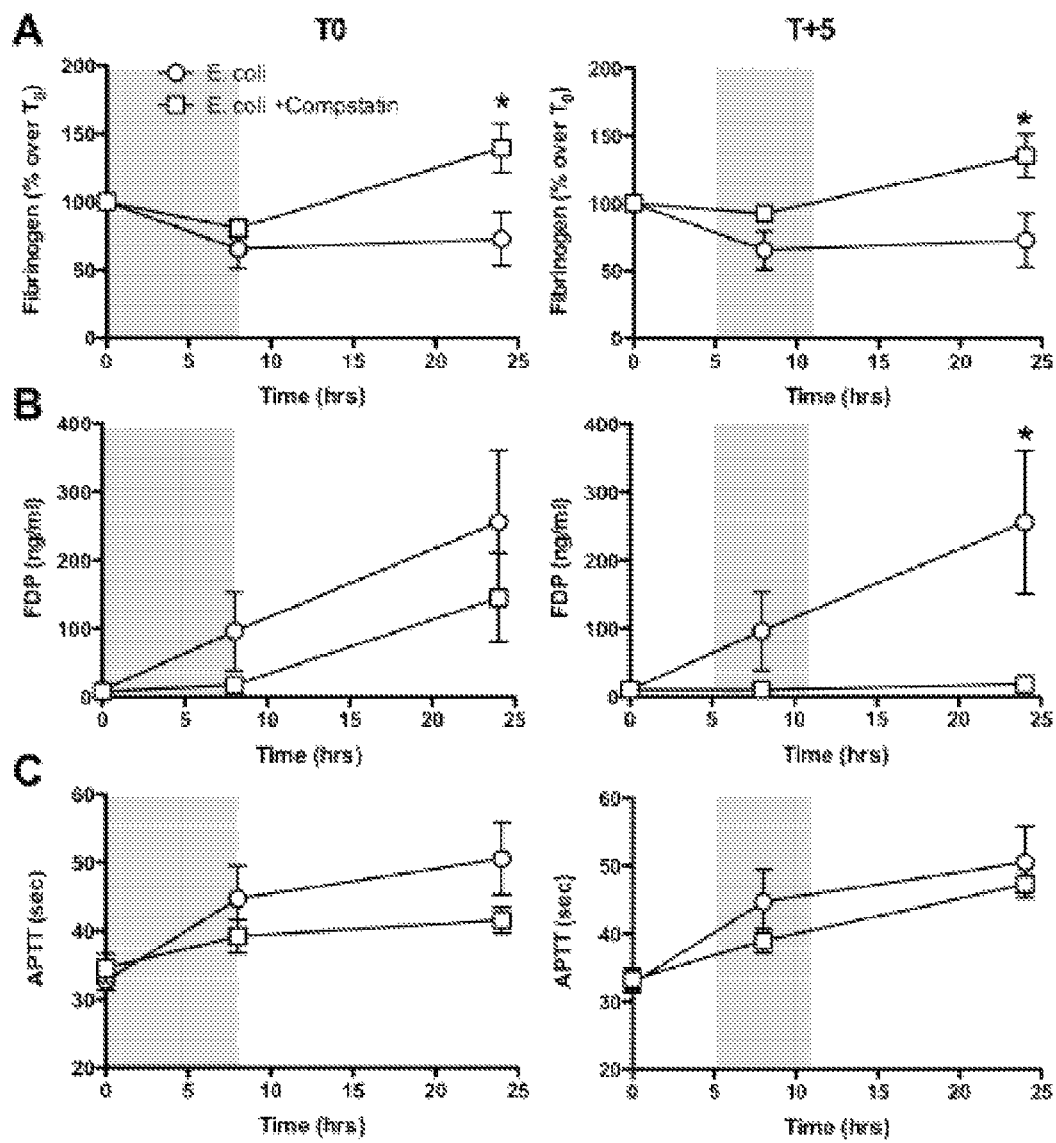
FIG. 4. Time-course of hemostatic parameters (A, fibrinogen; B, FDP; C, APTT) in the blood of baboons treated with Compstatin analog during the first (T0) and second (T+5) stages of experimental sepsis (baboon $LD_{50}$ model). Data are presented as mean±SEM; Two-tailed Student's t-test: * $p<0.05$.

*E. coli* infusion induced a gradual decrease of fibrinogen levels, especially during the first eight hours post-challenge (FIG. 4A). Compstatin analog treatment reduced fibrinogen consumption during this time-frame. Fibrinogen levels fully recovered and overshot the initial values after 24 hours, as compared with non-treated animals (FIG. 4A). Consistent with a reduction in the coagulopathic response, FDP levels were significantly lower (FIG. 4B) and the APTT was slightly decreased (FIG. 4C) in the treated animals.

Figure 5:
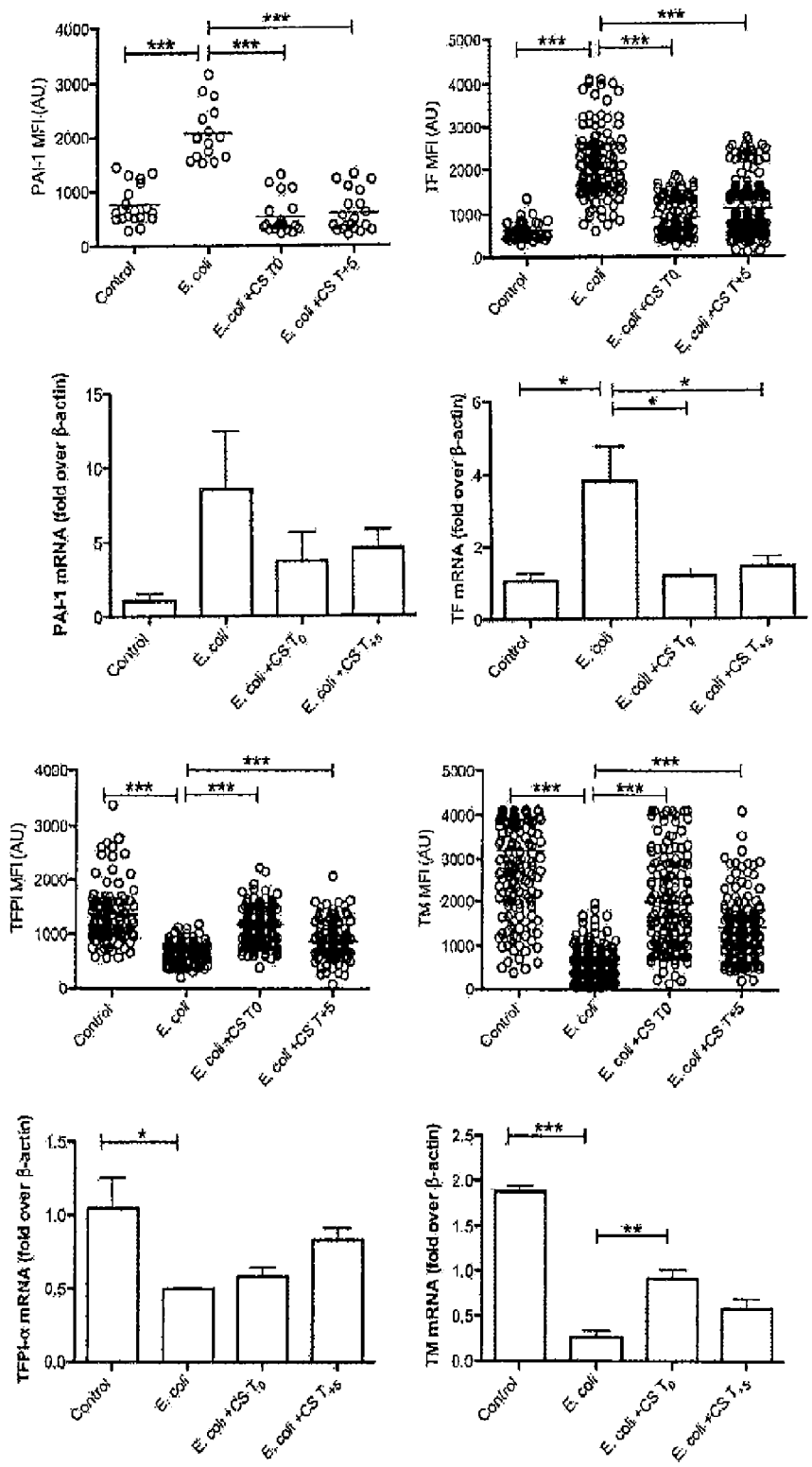
FIG. 5. Localization and quantitative analysis of hemostatic proteins in the lungs of baboons treated with a Compstatin analog during the first (T0) and second (T+5) stage of experimental sepsis ($LD_{50}$ model). Top panels: Scatter-plot representations of MFI of images (not shown) collected for PAI-1, tissue factor (TF), TFPI and thrombomodulin (TM) in healthy controls, septic baboons (E. coli), and septic baboons treated with Compstatin analog (CS) during the first (E. coli+ CS T0) or the second (E. coli+CS T+5) stage. Bottom panels: Histogram representation of mRNA expression for PAI-1, TF, TFPI and TM. Values indicate the mean±SEM of fold over beta-actin housekeeping gene. All data are presented as mean±SEM. One-way ANOVA with Dunnett's multi-comparison test: * $p<0.05$ $p<0.001$; * $p<0.0001$, compared with E. coli group FIG. 6. Time-course of organ function and biochemical markers in the blood of baboons treated with Compstatin analog during the first (T0) and second (T+5) stage of experimental sepsis ($LD_{50}$ model). A: Mean systemic arterial pressure (MSAP); B: creatinine; C: lactate dehydrogenase (LDH); D: alanine aminotransferase (ALT); E: aspartate transaminase (AST). Data are presented as mean±SEM; Two-tailed Student's t-test: * $p<0.05$,  $p<0.01$; * $p<0.001$.

Quantitative immunofluorescence analysis of lung cryosections stained for PAI-1, TF, TFPI and TM (FIG. 5A) demonstrated that *E. coli* sepsis markedly increased PAI-1 and TF and decreased TFPI and TM. Both early and late treatments with the Compstatin analog decreased *E. coli* induced TF and PAI-1 staining and protected against sepsis-induced down-regulation of TFPI and TM in endothelial cells (FIG. 5A). Immunocytochemistry data correlated well with the amount of mRNA transcripts of these proteins (FIG. 5B).

The decrease in TF expression in the lung of Compstatin analog treated animals correlated with the observed decrease in monocyte/macrophages infiltration. PAI-1 expression in endothelial cells and macrophages was down-regulated in Compstatin analog treated versus non-treated septic baboons. The changes described in the lung were consistently observed in other organs also. For example, PAI1 mRNA in liver was increased 22-fold (±9) by *E. coli* sepsis but only 8-fold (±8) in animals treated with the Compstatin analog at T0 and 4-fold (±0.8) at T+5 as compared to non-challenged controls (1±0.6) (all values are mean±SEM). Altogether, these data demonstrate that complement inhibition leads to decreased procoagulant activity and a better preserved endothelial anticoagulant function.

Example 5

Effects of Complement Inhibition Treatment on Plasma Cytokines

Nine of the 23 cytokines assayed increase markedly in the *E. coli* sepsis group. The effect of the Compstatin analog on the cytokines was marginal, except for a reduction observed for eotaxin and IL-6 with both the preventive and rescue therapy (data not shown).

Example 6

Figure 6:
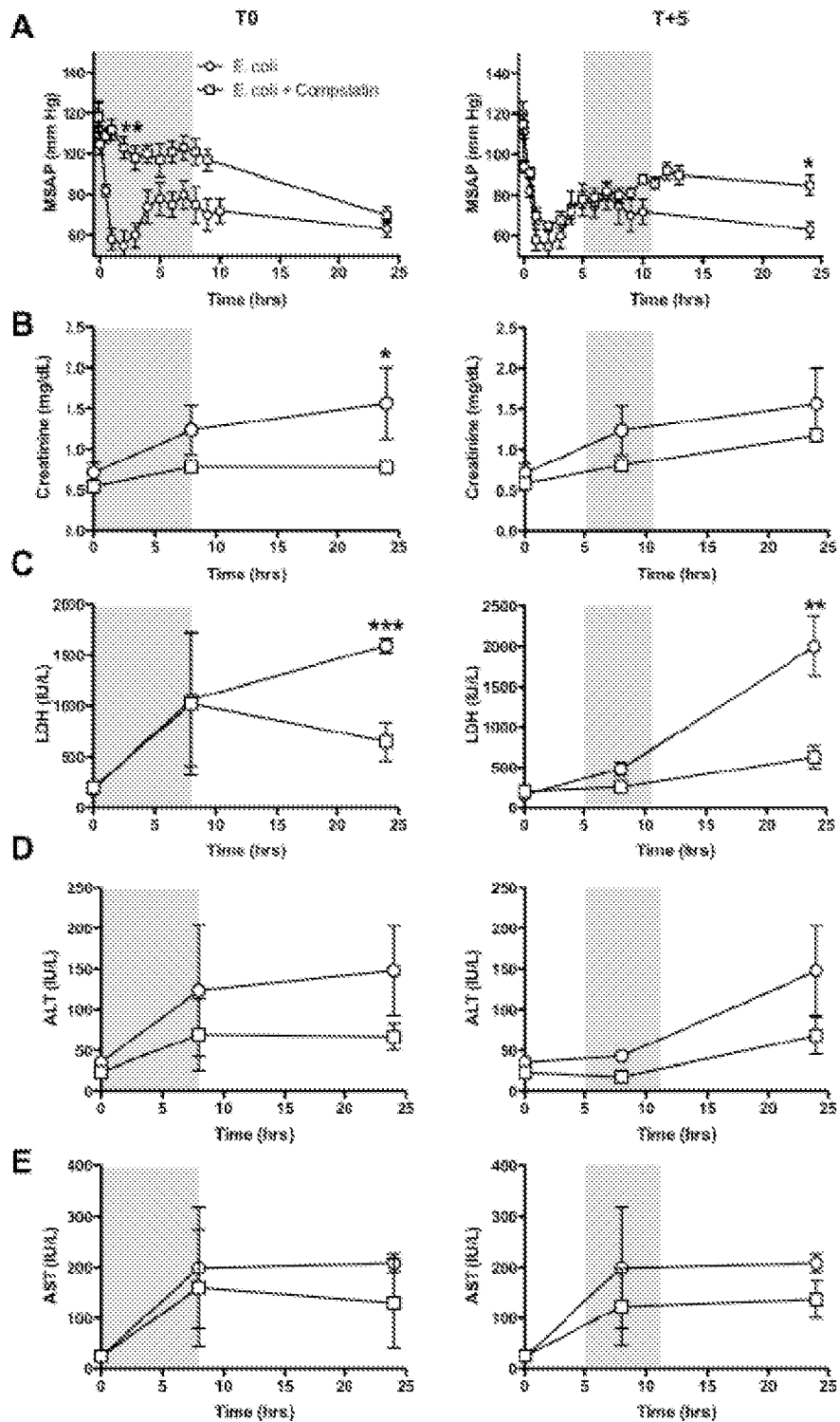

Effect of Complement Inhibition on Blood Pressure and Organ Preservation and Function Mean systemic arterial blood pressure decreased markedly in septic animals (FIG. 6A). Early Compstatin analog treatment virtually abolished this decrease. Treatment during the second stage led to higher recovery of the blood pressure in the late phase as compared with septic untreated baboons, despite the same degree of decrease in the early phase.

Figure 7:
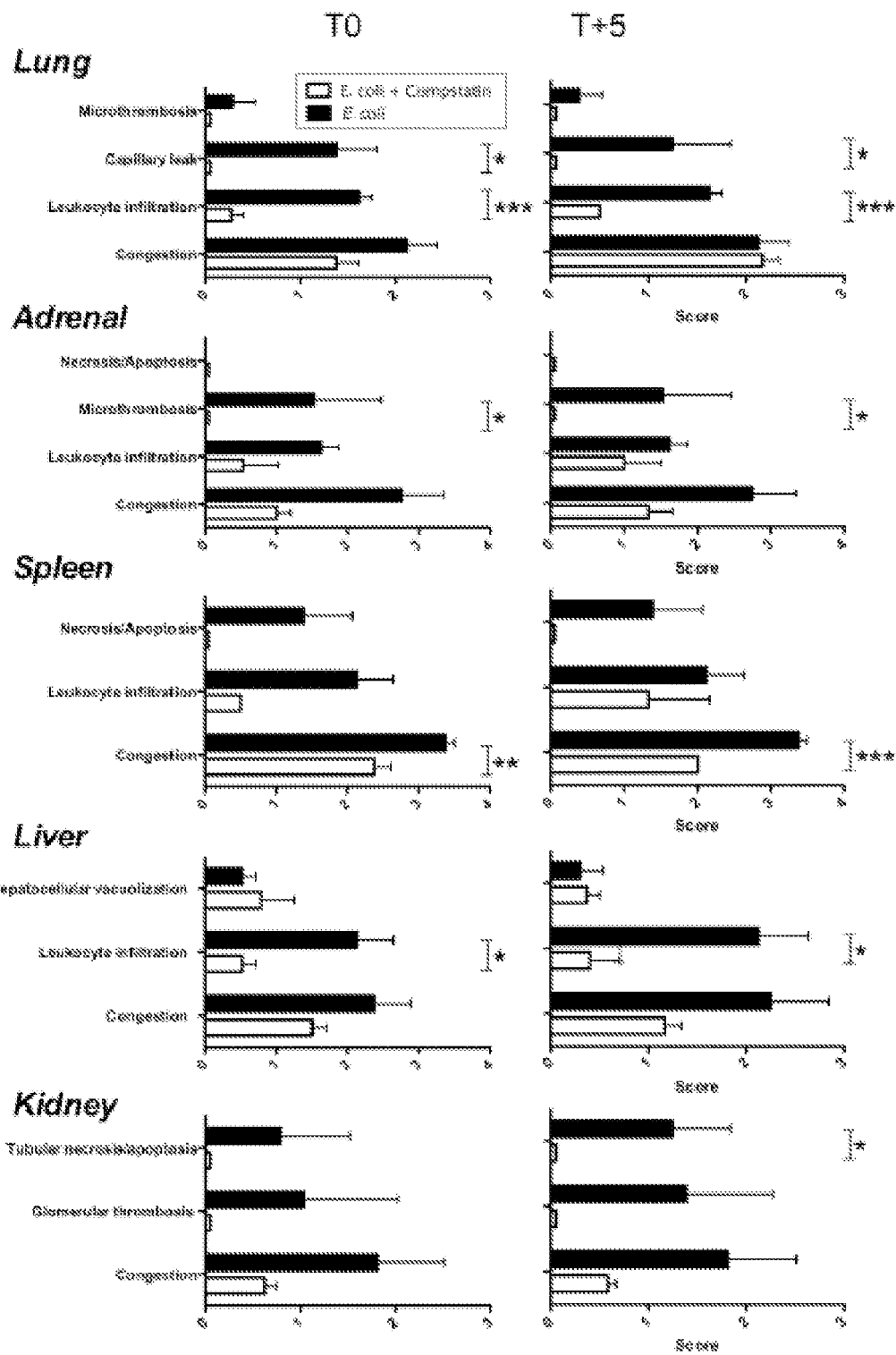
FIG. 7. Comparison of the histopathological changes in organs from septic animals with or without Compstatin analog treatment during the first (T0) or second (T+5) stage of experimental sepsis (baboon $LD_{50}$ model). The tissues were collected after euthanasia at T+24 hours. Evaluations of the parameters were performed in a blinded fashion and graded on a scale from 0 to 4, with 0 being normal and 4 being severe. The histopathologic changes of the tissues collected from the two Compstatin analog treated groups are significantly less severe than those of the E coli challenge group. $P<0.001$, with the exception of the lung congestion. Data are presented as mean±SEM. Two-tailed Student's t-test: * $p<0.05$;  $p<0.01$; * $p<0.001$.

To evaluate whether Compstatin analog administration could affect biochemical markers of organ damage, four markers of tissue injury were analyzed at T0, T+8 and T+24. Time-dependent changes in markers of organ function are presented in FIG. 6B-E. The creatinine, LDH, ALT and AST were increased by *E. coli* sepsis after 8 and 24 hrs postchallenge. The magnitude of the response for all four markers was lower in the two Compstatin analog treatment groups, as compared to non treated septic animals (FIG. 6B-E), indicating that complement inhibition attenuates kidney and liver injury. For pathological examination, all animals were euthanized after 24 hrs and tissues were removed for analysis within minutes after death to avoid autolytic postmortem changes. Histological analysis of organs confirmed that the Compstatin analog provided substantial organ-protection. The scoring of the histopathologic lesions of the lung, kidney, liver, adrenals and spleen is shown in FIG. 7. Differently from the non-treated group, Compstatin analog treated animals showed no obvious signs of thrombosis or capillary leak in the lungs, no or less tubular necrosis and glomerular thrombosis in the kidneys, lack of hepatocyte vacuolization and liver degeneration, less leukocyte infiltration in the lung, liver adrenals and spleen, and decreased cell death in adrenals and spleen. Immunostaining for cell specific markers showed a significant decrease in CD68 positive macrophages (FIG. 3C) without significant changes in the number of neutrophils (not shown).

Example 7

Effect of Compstatin Analog on Complement Activation and Survival in $LD_{100}$ Model of *E. coli* Sepsis in Baboons Reagents, Compstatin analog and live *E. coli* organisms were obtained or prepared as described in Example 1. *Papio cyanocephalus* baboons were infused with $2-3 \times 10^{10}$ CFU/kg live *E. coli* ($LD_{100}$ dose) as described (Taylor F B, Jr., et al., 2000, Blood 95: 1680-1686). The time point at which the infusion was started was indicated as T-0, a time point of n minutes or hours thereafter referred to as T+n minutes (or hours). The Compstatin analog was administered at three different concentrations as an intravenous bolus followed by continuous infusion.

Complement activity was measured in accordance with known methods. Survival time was also recorded.

Table 1 compares the percent complement activation and survival time of three baboons infused with $LD_{100}$ amounts of *E. coli* alone versus three baboons infused with increasing concentrations of Compstatin and $LD_{100}$ amounts of *E. coli*.

TABLE 1

| Animal # | Compstatin Treatment | | | % Complement Activation at T+120 min | Survival Time |
|---|---|---|---|---|---|
| | Total (mg) | Bolus | Infusion | | |
| 1 | 58 | 0.33 mg/kg T−0 1.74 mg/kg T+60 | 20 µg/min/ kg (8 hrs) | 0.6 | 31.5 hours |
| 2 | 78 | 1.0 mg/kg T−0 2.3 mg/kg T+60 | 20 µg/min/ kg (8 hrs) | 0.5 | 7.0 hours |

TABLE 1-continued

| Animal # | Compstatin Treatment | | | % Complement Activation at T+120 min | Survival Time |
|---|---|---|---|---|---|
| | Total (mg) | Bolus | Infusion | | |
| 3 | 760 | 10 mg/kg T-0 | 200 µg/min/kg (8 hrs) | 0.0 | 11.5 hours |
| 4 | 0 | | 0 | (Avg.) 2.8 | 34 hours |
| 5 | 0 | | 0 | | 70 hours |
| 6 | 0 | | 0 | | >7 days |

As can be seen, the animal receiving the highest concentration of Compstatin exhibited complete inhibition of complement activation by T+120 minutes, while the animals receiving the lesser concentrations exhibited substantial inhibition of complement activation by T+120 minutes. The Compstatin-treated animals died within a few hours, while the untreated animals survived longer. It is noted in this regard that none of the animals received antibiotic treatment, whereas patients in clinical settings would be treated with antibiotics immediately upon diagnosis of severe sepsis. Since complement activation is a first line of defense against pathogen invasion, the Compstatin-induced inhibition of complement activation without concomitant antibiotic therapy may explain the limited survival time of animals in this $LD_{100}$ model.

Example 8

Role of Extracellular Histones in the $LD_{50}$ E. coli Sepsis Model of Organ Failure in Baboons To determine if extracellular histones play a role in the extravascular stage of sepsis in the $LD_{50}$ E. coli sepsis model, baboons were infused with successive two-hour infusions of histones at a rate of 70, 350 and 700 µg/kg/min, or were administered, beginning at T-0, a two-hour infusion of 70/µg/kg/min histones and 35 µg/kg/min DNA respectively, followed at T+2 hr with a one-hour infusion of 350 µg/kg/min histones and 175 µg/kg/min DNA respectively. Complement activation was measured via generation of C5b9. In each instance, infusion with histones led to complement activation. Increases in histone infusion resulted in concomitant, proportionate, increases in complement activation. Histological examinations confirmed the deposition of complement activation products in tissues as a result of the histone infusions. Inasmuch as histones were previously shown to be released into circulation during sepsis (Xu et al., 2009), these results indicate that circulating histones play a role in the complement activation that occurs in the extravascular stage of sepsis.

The present invention is not limited to the embodiments described and exemplified above, but is capable of variation and modification within the scope of the appended claims.

What is claimed:

1. A method for treating extravascular cell, tissue or organ injury following a sepsis-inducing infection in an individual, the method comprising:
   (a) identifying an individual with stage 1 sepsis resulting from infection, wherein the stage 1 sepsis is characterized by one or both of: (i) disseminated intravascular coagulation (DIC) and (ii) hypoperfusion of vital organs;
   (b) detecting in the individual one or more of: (i) increased blood pressure compared to the stage 1 sepsis; (ii) reperfusion of vital organs; and (iii) persistent or worsening organ failure despite adequate blood pressure, thereby determining the onset of stage 2 sepsis; and
   (c) at the time of or after the determining of onset of stage 2 sepsis, administering to the individual a therapeutically effective amount of a complement C3 inhibitor comprising compstatin or a compstatin analog selected from the group consisting of SEQ ID NO:1, SEQ ID NO.:2, SEQ ID NO:3, SEQ ID NO:4 and any combination thereof, wherein the administering of the C3 inhibitor reduces or prevents the extravascular cell, tissue or organ injury in the individual.

2. The method of claim 1, wherein the administering of the C3 inhibitor is continued until at least one indicator of the reduction or prevention of the extravascular cell, tissue or organ injury is detected.

3. The method of claim 2, wherein the indicator of the reduction or prevention of the extravascular cell, tissue or organ injury is selected from one or more of (1) reduction in blood or tissue biomarkers of complement activation; (2) reduced leucopenia or thrombocytopenia; (3) lowered accumulation of macrophages or platelets in organs; (4) improvement in cardiac function; (5) decrease in biochemical markers of kidney or liver damage; and (6) histological analysis of organs showing decreased microvascular thrombosis, improved vascular barrier function, or less leukocyte infiltration and cell death.

4. The method of claim 1 wherein the individual is human.

5. The method of claim 1, wherein the C3 inhibitor is administered systemically.

6. The method of claim 1, wherein the C3 inhibitor is administered locally to a tissue or organ.

7. The method of claim 1, wherein the C3 inhibitor is administered concurrently with, or sequentially before or after, at least one other treatment for the stage 2 sepsis-related extravascular cell, tissue or organ injury.

8. The method of claim 1, wherein the C3 inhibitor is administered concurrently with or after administration of one or more agents or regimens for treating stage 1 of sepsis.

9. The method of claim 8, wherein the agent for treating stage 1 of sepsis is selected from one or more of activated protein C (APC), a mutant form of APC, an APC precursor, an APC cofactor, or any combination thereof.

10. A method of treating sepsis, comprising:
    (a) identifying an individual with stage 1 sepsis resulting from infection, wherein the stage 1 sepsis is characterized by one or both of: (i) disseminated intravascular coagulation (DIC) and (ii) hypoperfusion of vital organs;
    (b) administering to the individual one or more agents effective to treat the stage 1 sepsis;
    (c) detecting in the individual one or more of: (i) increased blood pressure compared to the stage 1 sepsis; (ii) reperfusion of vital organs; and (iii) persistent or worsening organ failure despite adequate blood pressure, thereby determining onset of stage 2 sepsis; and
    (d) at the same time or after determining the onset of the stage 2 sepsis, administering to the individual a therapeutically effective amount of a complement C3 inhibitor comprising compstatin or a compstatin analog selected from the group consisting of SEQ ID NO:1, SEQ ID NO:2, SEQ ID NO:3, SEQ ID NO:4 and any combination thereof,
    wherein the administering of the one or more agents effective to treat stage 1 sepsis, combined with the administering of a C3 inhibitor at or after onset of the stage 2 sepsis results in treating of the sepsis.

11. The method of claim 10, wherein the agent effective to treat stage 1 sepsis is activated protein C (APC), a mutant form of APC, an APC precursor, an APC cofactor, or any combination thereof, and the C3 inhibitor is Compstatin, a Compstatin analog, or any combination thereof.

* * * * *